US00PP31418P2

(12) United States Plant Patent
Smit

(10) Patent No.: US PP31,418 P2
(45) Date of Patent: Jan. 28, 2020

(54) ***PEPEROMIA* PLANT NAMED 'MOONLIGHT'**

(50) Latin Name: *Peperomia caperata*
Varietal Denomination: Moonlight

(71) Applicant: Obed Jacob Smit, Sappemeer (NL)

(72) Inventor: Obed Jacob Smit, Sappemeer (NL)

(73) Assignee: Eden CollecTion B.V., Sappemeer (NL)

( * ) Notice: Subject to any disclaimer, the term of this patent is extended or adjusted under 35 U.S.C. 154(b) by 0 days.

(21) Appl. No.: 16/350,743

(22) Filed: Dec. 31, 2018

(51) Int. Cl.
*A01H 5/12* (2018.01)

(52) U.S. Cl.
USPC ..... Plt./373

(58) Field of Classification Search
USPC ..... Plt./373
CPC ..... A01H 6/00; A01H 5/02; A01H 5/12
See application file for complete search history.

*Primary Examiner* — Keith O. Robinson

(57) ABSTRACT

A new cultivar of *Peperomia* plant named 'Moonlight' that is characterized by a large overall size and grey-green leaves with green veins.

1 Drawing Sheet

Botanical classification: *Peperomia caperata.*
Variety denomination: 'Moonlight'.

BACKGROUND OF THE INVENTION

The present invention relates to a new and distinct cultivar of *Peperomia* plant botanically known as *Peperomia caperata* and hereinafter referred to by the cultivar name 'Moonlight'.

'Moonlight' originated from the crossing of the female or seed parent, an unnamed *Peperomia caperata* cultivar and the male or pollen parent, an unnamed *Peperomia caperata* cultivar. The crossing was conducted in 2013 in Sappemeer, Netherlands. The resulting seeds were subsequently planted and grown. The cultivar 'Moonlight' was selected by the inventor in 2014 in a controlled environment as a single plant within the progeny of the stated cross in a cultivated area of Sappemeer, Netherlands.

Asexual reproduction of the new cultivar 'Moonlight' first occurred by leaf cuttings in 2014 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Peperomia* cultivar 'Moonlight'. These traits in combination distinguish 'Moonlight' as a new and distinct cultivar apart from other existing varieties of *Peperomia* known by the inventor.

1. Peperomia 'Moonlight' exhibits a large overall size.
2. Peperomia 'Moonlight' exhibits grey-green leaves with green veins.

The closest comparison cultivars are *Peperomia* 'Schumi Red' (not patented) and *Peperomia* 'Napoli Nights' (U.S. Plant Pat. No. 29,416). 'Moonlight' is distinguishable from 'Schumi Red' by the following characteristics:

1. *Peperomia* 'Moonlight' exhibits grey-green leaves with green veins. In comparison, the leaves of 'Schumi Red' are red.

2. *Peperomia* 'Moonlight' exhibits yellow-green petioles with grey-red stripes. In comparison, the petioles of 'Schumi Red' are red.
3. *Peperomia* 'Moonlight' exhibits a less compact plant habit than the plant habit of 'Schumi Red'.

'Moonlight' is distinguishable from 'Napoli Nights' by the following characteristics:

1. *Peperomia* 'Moonlight' exhibits grey-green leaves with green veins. In comparison, the leaves of 'Napoli Nights' are grey-green on the upper surface and pink-red on the lower surface.

'Moonlight' is distinguishable from the female parent plant, by the following characteristics:

1. The leaves of 'Moonlight' are grey-green with green veins. In comparison, the leaves of the female parent plant are green.
2. The leaves of 'Moonlight' have furrowed veins. In comparison, the leaves of the female parent plant do not have furrowed veins.

'Moonlight' is distinguishable from the male parent plant by the following characteristics:

1. The leaves of 'Moonlight' are grey-green with green veins. In comparison, the leaves of the male parent plant are pale grey.

BRIEF DESCRIPTION OF THE DRAWING

The accompanying photograph illustrates the distinguishing traits of *Peperomia* 'Moonlight'. The photograph shows an overall view of a 52 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Peperomia* cultivar named 'Moonlight'. Data was collected in Sappemeer, Netherlands from 52 week old plants grown in a glass greenhouse in 13 cm. diameter containers. The time of year was Summer and the temperature range was 20-23 degrees Centigrade during the day and 18-20 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'Moonlight' has not been tested under all possible conditions and phenotypic differences may be observed with variations in environmental, climatic, and cultural conditions, however, without any variance in genotype.

Botanical classification: *Peperomia caperata* 'Moonlight'.

Annual or perennial: Perennial.

Parentage: 'Moonlight' is a hybrid of the female parent, an unnamed *Peperomia caperata* cultivar and the male parent an unnamed *Peperomia caperata* cultivar.

Plant type: Potted plant.

Growth habit: Rosette.

Plant shape: Flattened globe shaped.

Suitable container size: 7 cm. pots or larger.

Plant height to top of foliage: Average 17.0 cm.

Plant height to top of floral plane: Average 29.7 cm.

Plant width: Average 40.8 cm.

Vigor: Moderate.

Growth rate: Moderate.

Low temperature tolerance: 5° Centigrade.

High temperature tolerance: 35° Centigrade.

Propagation: Leaf cuttings.

Time to initiate roots (summer): 10 days at 18 to 20° C.

Time to initiate roots (winter): 14 days at 18 to 20° C.

Time to produce a rooted cutting (summer): 80 days at 18 to 20° C.

Time to produce a rooted cutting (winter): 100 days at 18 to 20° C.

Crop time: Approximately 24 weeks in Sappemeer, Netherlands.

Root system: Fibrous.

Plant fragrance: None.

Stem:

- *Branching habit.*—Short thick stems branching into rosettes of leaves.
- *Pinching.*—Not required.
- *Number of main stems per plant.*—Average 12.
- *Number of lateral branches per plant.*—Average 40.
- *Lateral branch dimensions.*—Average 2.0 cm. in length and 0.8 cm. in width.
- *Internode length.*—Less than 0.1 cm.
- *Stem appearance.*—Succulent.
- *Stem shape.*—Rounded.
- *Stem texture.*—Smooth.
- *Stem luster.*—Slightly glossy.
- *Stem pubescence.*—Absent.
- *Stem angle.*—Average 20 degrees.
- *Stem strength.*—Moderately strong.
- *Stem color* (*young*).—148D.
- *Stem color* (*mature*).—N148D.
- *Internode color.*—N148D.

Foliage:

- *Leaf arrangement.*—Alternate.
- *Compound or single.*—Single.
- *Quantity of leaves per lateral branch.*—Average 10.
- *Leaf shape.*—Ovate.
- *Leaf aspect.*—Very slightly convex.
- *Leaf apex.*—Broad acute to broad apiculate.
- *Leaf base.*—Cordate, lobes free to touching.
- *Leaf dimensions.*—Average 6.5 cm. in length and 5.5 cm. in width.
- *Texture.*—Glabrous, moderately leathery (both surfaces).
- *Leaf luster upper surface.*—Glossy.
- *Leaf luster lower surface.*—Matte.
- *Pubescence.*—Absent (both surfaces).
- *Leaf margin.*—Entire.
- *Leaf lobed.*—Not lobed.
- *Leaf rugose.*—Not rugose (both surfaces).
- *Venation pattern.*—Parallel, strongly furrowed.
- *Young leaf color* (*upper surface*).—191A, veins 143A.
- *Young leaf color* (*lower surface*).—138C, veins 138B.
- *Mature leaf color* (*upper surface*).—189A, N189B and 191A.
- *Mature leaf color* (*lower surface*).—148C and N148C.
- *Vein color* (*upper surface*).—Between NN137A and N189A.
- *Vein color* (*lower surface*).—147B.

Petiole:

- *Petiole dimensions.*—Average 13.9 cm. in length and 0.35 cm. in diameter.
- *Petiole texture.*—Glabrous.
- *Petiole luster.*—Moderately glossy on both sides.
- *Petiole pubescence.*—Absent.
- *Petiole strength.*—Low.
- *Petiole color.*—148C with fine stripes 182A.

Flower:

- *Inflorescence type.*—Axillary spike.
- *Inflorescence dimensions.*—Average 13.6 cm. in length and 0.3 cm. in diameter, inflorescences occasionally cleft at top, diameter when cleft 1.7 cm.
- *Quantity of flowers per inflorescence.*—Average over 10,000.
- *Quantity of flowers per plant.*—Average over 100,000.
- *Quantity of buds per plant.*—Average over 100,000.
- *Quantity of flowers and buds per plant.*—Average over 200,000.
- *Fragrance.*—None.
- *Bud length.*—Average 0.2 mm.
- *Bud diameter.*—Average 0.2 mm.
- *Bud shape.*—Globose.
- *Bud texture.*—Glabrous.
- *Bud luster.*—Slightly glossy.
- *Bud color.*—144B.
- *Flower type and form.*—Flowers have no petals or sepals and consist of two stamens and one pistil.
- *Flower aspect.*—Outward.
- *Flower shape.*—Rotate, two stamens and one pistil.
- *Flower dimensions.*—Average 0.75 mm. in diameter and 0.5 mm. in height.
- *Flower longevity.*—Approximately 1 month.
- *Persistent or self-cleaning.*—Self-cleaning.

Peduncle:

- *Peduncle dimensions.*—Average 14.5 cm. in length and 0.3 cm. in diameter.
- *Peduncle angle.*—25 degrees from vertical.
- *Peduncle strength.*—Moderately weak.
- *Peduncle texture.*—Smooth.
- *Peduncle luster.*—Moderately glossy.
- *Peduncle color.*—195B with fine stripes 182A.

Reproductive organs:

- *Stamen number.*—2.
- *Anther shape.*—Kidney shaped.
- *Anther length.*—0.2 mm.

*Anther width.*—0.1 mm.
*Anther color.*—200A.
*Filament length.*—0.1 mm.
*Filament color.*—143B.
*Amount of pollen.*—Low.
*Pollen color.*—155A.
*Number of pistils.*—1.
*Pistil length.*—0.1 mm.
*Stigma shape.*—Flattened, ovate.
*Stigma dimensions.*—0.05 mm. in length and 0.15 mm. in diameter.
*Stigma color.*—143C.
*Style.*—Not visible.
*Ovary color.*—144A.

Fruit and seed: 'Moonlight' has not produced fruit or seed to date.

Disease and pest resistance: Disease and pest resistance has not been observed.

The invention claimed is:

1. A new and distinct variety of *Peperomia* plant named 'Moonlight' as described and illustrated.

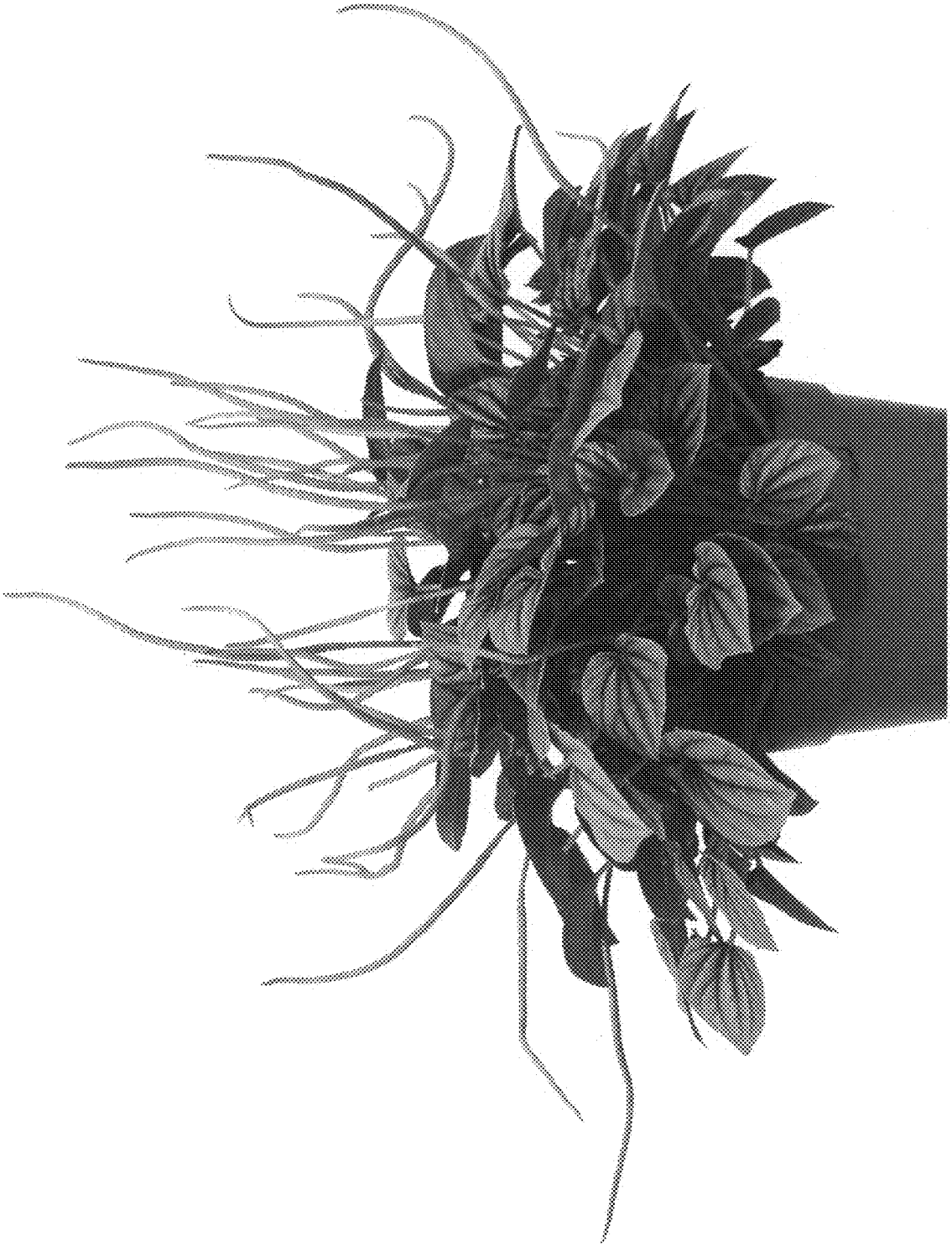

* * * * *